(12) United States Patent
Hietala

(10) Patent No.: US 11,366,056 B2
(45) Date of Patent: Jun. 21, 2022

(54) RESPIRATORY GAS ANALYZER AND A BEAM SPLITTER THEREFOR

(71) Applicant: GE Precision Healthcare LLC, Wauwatosa, WI (US)

(72) Inventor: Mika Harri Juhani Hietala, Espoo (FI)

(73) Assignee: GE Precision Healthcare LLC, Wauwatosa, WI (US)

(*) Notice: Subject to any disclaimer, the term of this patent is extended or adjusted under 35 U.S.C. 154(b) by 377 days.

(21) Appl. No.: 16/589,983

(22) Filed: Oct. 1, 2019

(65) Prior Publication Data

US 2021/0096064 A1    Apr. 1, 2021

(51) Int. Cl.

| | |
|---|---|
| *G01N 21/35* | (2014.01) |
| *G01N 21/31* | (2006.01) |
| *G01N 33/497* | (2006.01) |
| *A61B 5/08* | (2006.01) |
| *A61B 5/097* | (2006.01) |
| *G02B 5/20* | (2006.01) |
| *G01J 3/02* | (2006.01) |
| *G01J 3/42* | (2006.01) |
| *G01J 3/36* | (2006.01) |
| *G01N 21/3504* | (2014.01) |
| *A61B 5/083* | (2006.01) |
| *G01J 3/427* | (2006.01) |
| *A61N 5/06* | (2006.01) |
| *G01J 3/12* | (2006.01) |

(52) U.S. Cl.
CPC ....... *G01N 21/3504* (2013.01); *A61B 5/0836* (2013.01); *A61B 5/097* (2013.01); *G01J 3/021* (2013.01); *G01J 3/36* (2013.01); *G01J 3/427* (2013.01); *G01N 21/314* (2013.01); *G01N 33/497* (2013.01); *G02B 5/208* (2013.01); *A61N 2005/0626* (2013.01); *G01J 2003/1213* (2013.01); *G01N 2021/3137* (2013.01); *G01N 2021/3166* (2013.01); *G01N 2033/4975* (2013.01)

(58) Field of Classification Search
CPC ............ A61B 5/097; A61B 5/0836; A61N 2005/0626; G01J 3/021; G01J 3/36; G01J 3/427; G01J 2003/1213; G01N 21/3504; G01N 33/497; G01N 2021/3137; G01N 2021/3166; G01N 2033/4975; G02B 5/208
See application file for complete search history.

(56) References Cited

U.S. PATENT DOCUMENTS

| | | |
|---|---|---|
| 6,828,910 B2 | 12/2004 | VanRyzin et al. |
| 6,954,702 B2 | 10/2005 | Pierry et al. |
| (Continued) | | |

*Primary Examiner* — Mark R Gaworecki
(74) *Attorney, Agent, or Firm* — Andrus Intellectual Property Law, LLP

(57) ABSTRACT

A gas analyzer for measuring a respiratory gas component includes an emitter that emits two different wavelengths of infrared (IR) radiation in to a measurement chamber containing a respiratory gas, wherein the two different wavelengths include a first IR wavelength and a second IR wavelength. The gas analyzer further includes a first IR detector, a second IR detector, and a beam splitter. The beam splitter is configured to receive the two different wavelengths of radiation emitted by the emitter and to split the two wavelengths of radiation so as to reflect the first IR wavelength to the first IR detector and reflect the second IR wavelength to the second IR detector.

17 Claims, 3 Drawing Sheets

(56) References Cited

U.S. PATENT DOCUMENTS

| | | |
|---|---|---|
| 8,642,966 B2 | 2/2014 | Weckstrom et al. |
| 2007/0217009 A1* | 9/2007 | Richter .................... G01J 3/02 |
| | | 359/485.02 |
| 2010/0036272 A1 | 2/2010 | Mace et al. |
| 2012/0097852 A1* | 4/2012 | Weckstrom ........ G01N 21/3504 |
| | | 250/343 |

* cited by examiner

RESPIRATORY GAS ANALYZER AND A BEAM SPLITTER THEREFOR

BACKGROUND

The present disclosure generally relates to a gas analyzer for measuring a respiratory gas component, and more particularly to a gas analyzer having a beam splitter configured to split infrared (IR) radiation based on wavelength.

In anesthesia and in intensive care, the condition of a patient is often monitored by analyzing the gas inhaled and exhaled by the patient for its content. For this reason, either a small portion of the respiratory gas is delivered to a gas analyzer or the gas analyzer is directly connected to the respiratory circuit. In a non-dispersive infrared (NDIR) gas analyzer the measurement is based on the absorption of infrared (IR) radiation in the gas sample. A radiation source directs a beam of infrared radiation through a measuring chamber to a radiation detector whose output signal depends on the strength of the absorption of the radiation in the sample gas.

The radiation source typically comprises an electrically heated filament or surface area and radiation collecting optics and emits radiation within a spectral region. The gas sample to be analyzed, i.e. the sample gas, is fed through the measuring chamber, whereupon the gas mixture is included in the chamber for analysis. The measuring chamber can be a tubular space provided with entrance and exit windows that are transparent at the measurement wavelength and with inlet and outlet for the sample gas. Radiation is absorbed by the gas sample when passing through the measuring chamber.

The radiation detector generates an electrical signal that depends on the radiation power falling on its sensitive area. The detector type in a gas analyzer depends on its measurement wavelength. For measurement within a broad spectral range, a thermal detector is convenient because its sensitivity only depends on the efficiency of the conversion of radiation to heat. To make the detector's output signal sensitive to a certain gas component, the wavelength band of the radiation coming to the detector is selected so that the gas component absorbs radiation within it. This selection is made using an optical bandpass filter whose bandwidth is typically 1%-2% of the center wavelength.

Gas analyzers can be configured to measure different gas components. The absorption of the gas sample is measured at a wavelength band selected to match the absorption spectra of the gas component(s) of interest. Measurement of more than one gas component can be accomplished by using one radiation detector and by changing the optical bandpass filters on the optical path in succession. It is also possible to use several radiation detectors, combined with corresponding bandpass filters.

In addition to these measurement detectors, there may be one or more reference detectors. In the clinically used gas analyzer of mainstream type, the whole volume or at least the main portion of the breathing air or gas mixture flows through the analyzer and its measuring chamber. Because the measuring chamber is in the breathing circuit, it is easily contaminated by mucus or condensed water. Sidestream measurement environments pose similar issues. Thus, it is necessary to use one or more reference beams in order to have a baseline that depicts the absorption and impact of the airway adapter material and the contamination factors. The reference detectors are used to provide such a reference.

Different respiratory gases have widely spaced wavelength regions of absorption. Carbon dioxide and nitrous oxide can be measured between 3900 nm and 4600 nm whereas anesthetic agents absorb in the 8000 nm to 10000 nm region.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a gas analyzer for measuring a respiratory gas component includes an emitter that emits two different wavelengths of infrared (IR) radiation in to a measurement chamber containing a respiratory gas, wherein the two different wavelengths include a first IR wavelength and a second IR wavelength. The gas analyzer further includes a first IR detector, a second IR detector, and a beam splitter. The beam splitter is configured to receive the two different wavelengths of radiation emitted by the emitter and to split the two wavelengths of radiation so as to reflect the first IR wavelength to the first IR detector and reflect the second IR wavelength to the second IR detector.

One embodiment of the beam splitter for a respiratory gas analyzer includes an IR filter surface configured to pass a first IR wavelength and to reflect a second IR wavelength and a mirror positioned behind the IR filter that is configured to reflect the second IR wavelength. The beam splitter is configured such that it reflects the first IR wavelength to a first IR detector and reflects the second IR wavelength to a second IR detector.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
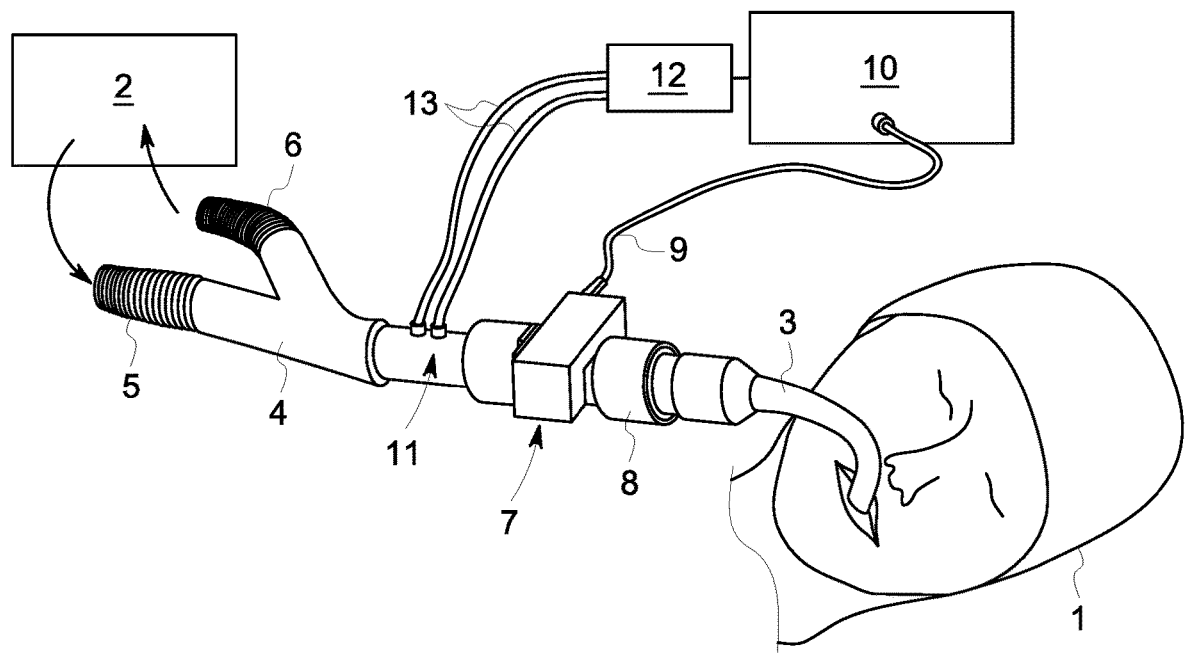
FIG. 1 illustrates a mainstream gas analyzer connected to the ventilation circuit of the patient.

As described above, there are generally two types of respiratory gas measurement devices, including sidestream devices that divert a sample of gas and measure the contents thereof and mainstream devices that conduct measurements directly across the respiratory gas channel within the respiratory circuit connected to the patient. The disclosed gas analyzer can be utilized in either one of a sidestream gas analyzer or a mainstream gas analyzer.

Gas analyzers, or gas measurement devices, that utilize infrared measurement typically include an infrared source, a measurement chamber with windows, and one or more detectors. The infrared source generates infrared radiation through the measurement chamber and the detector senses the infrared radiation and its variation on the other side of the sample chamber. As described above, gas analyzers and measurement devices may utilize a reference detector in order to identify the reference signal representing the maximum amount of transmitted radiation through the measurement chamber—i.e., if none of the radiation were absorbed by the measured gas. This is used as a reference value for comparison to the measurement and thus to be able to measure gas concentrations. The gas concentration is calculated using the relationship between the gas and reference detector signals.

The reference signal is comprised of one or more reference wavelengths that are not absorbed by the measured gas or other gases in the system in order to have a baseline that depicts the absorption and impact of the airway adapter material and the contamination factors. Reference detectors are used to provide such a reference, where the reference signal is filtered (such as via a bandpass filter) in order to provide only the reference wavelengths to the reference detector. Reference detectors receive radiation from the radiation source at wavelength bands where the sample gas is known to have little or no absorption. The reference wavelength is thus different from the measurement wavelength, but may be relatively close to the measurement wavelength so that it is equally impacted by the measurement environment and the contaminant, such as moisture, etc. For example, the sample chamber windows make it dirty or water droplets may accumulate thereon, particularly in the case of a mainstream airway adapter and measurement device. These impurities impact the IR signal utilized to measure particular gas contents, such as $CO_2$, $N_2O$, or anesthetic agents. The impurities cause a drop in the signal received at the detector.

Gas analyzers having a reference detector may include a beam splitter, which divides the infrared radiation transmitted through the measurement chamber to the gas detector and the reference detector. Thereby, if there are impurities in the windows of the measurement chamber, such impurities impact both the measurement beam and the reference beam such that it is sensed by both detectors. The traditional way of implementing a beam splitter is to use a component that reflects 50% of the radiation transmitted through the measurement chamber and passes 50% of the signal. This type of beam splitter splits the amplitude of the signal, where half of the signal is used for determining the gas concentration and the other half is used utilized for reference. The relevant wavelengths are then isolated at the detector, such as by utilizing bandpass filters as just described.

The inventor has recognized that this amplitude-splitting type of beam splitter is suboptimal because only half of the generated radiation gets sensed by either one of the detectors. Thus, 50% of the signal is lost. Thus, it can be difficult to generate a sufficiently strong infrared signal in order to provide sufficient amplitude to each of the measurement and reference detectors in order to provide reliable gas concentration measurement. Moreover, the inventor has recognized that current beam splitter products are sensitive to production variabilities where manufacturing tolerances must be very tight in order to provide consistent and reliable measurement functionality.

In view of the foregoing problems and challenges recognized by the inventor, the disclosed gas analyzer and beam splitter were developed which utilizes an IR filter and is configured to split emitted IR radiation based on wavelength, rather than amplitude. Specifically, the beam splitter includes an IR filter that passes one IR wavelength and reflects another. For example, the IR filter may be configured to pass the measurement IR wavelength and reflect the reference IR wavelength. Alternatively, the IR filter may be configured to pass the reference IR wavelength and reflect the measurement IR wavelength. A mirror is positioned behind the IR filter and configured to reflect the wavelength that passes through the IR filter. The IR filter material has a material-specific refraction index and a specified thickness such that the beam splitter causes the two reflected IR signals to be transmitted along parallel paths separated by an offset distance such that the split wavelengths hit respective detector chips placed adjacent to one another.

In various embodiments, the IR filter may be a high pass infrared filter or a low pass infrared filter. The disclosed beam splitter enables transmission of most of the total radiation passed through the measurement chamber to be reflected to each of the detector chips. In one embodiment, 90% of the signal that reaches the beam splitter is received at the respective detector chip and at least 70% of the IR wavelength that reaches the beam splitter is received at the respective detector chip. These percentages are dependent on the materials and construction of the beam splitter, but in any event are higher than the 50% provided by the traditional amplitude-splitting beam splitter.

Thus, the disclosed beam splitter provides a better signal to each detector using the same emission power of the IR source, and may even enable utilization of decreased emission power compared to amplitude-splitting-type gas detectors. Thus, the lifetime of the IR source may be increased. Moreover, IR sources generate heat, which can be unwanted, particularly for mainstream devices which are placed close to the patient. The use of lower emission power enabled by the disclosed system will also decrease the amount of heat produced by the IR source. Finally, the disclosed beam splitter provides an easier construction because both reflecting surfaces are in the same component. Thus, tighter manufacturing tolerances can be met since, unlike the prior art beam splitter, multiple separate components do not need to be positioned with respect to one another. Finally, the disclosed beam splitter is compact compared to prior art beam splitters, and thus enables manufacture of a smaller gas analyzer.

A respiratory circuit with a medical gas analyzer is shown in FIG. 1. A patient 1 is connected to a ventilator 2 using an intubation tube 3, a Y-piece 4, an inspiratory limb 5, and an expiratory limb 6. A gas analyzer 7 which may comprise an adapter 8 is connected to the intubation tube. The gas analyzer 7 in FIG. 1 is a so-called mainstream gas analyzer measuring gases flowing between the ventilator 2 and the patient 1 without withdrawing samples of the gas to a separate gas analyzer such as a sidestream gas analyzer at a distance from the flow between the ventilator 2 and the patient 1 (see e.g., FIG. 3). This same gas analyzer technology is also utilized in sidestream gas analyzers (see FIG. 3). The analyzer shown in FIG. 1 is electrically connected via cable 9 to the patient monitor 10. The gas component measured may be carbon dioxide ($CO_2$), nitrous oxide ($N_2O$), or any of the volatile anesthetic agents halothane, enflurane, isoflurane, desflurane and sevoflurane. Additionally, there may be a spirometry adapter 11 for measuring the gas flow in the respiratory circuit. In this example, the sensor 12 is located at the distal end of two pressure relying tubes 13. The spirometry sensor may be separately connected as in FIG. 1 or it can be integrated into the mainstream gas analyzer.

Figure 2:
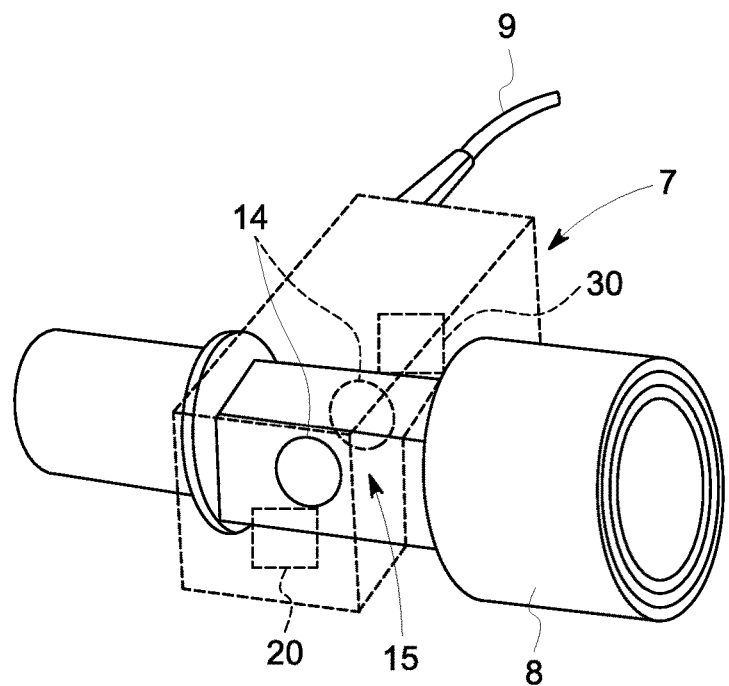
FIG. 2 shows an airway adapter and a mainstream gas analyzer connected thereto.

In FIG. 2, a close-up of the gas analyzer 7 is depicted in order to better show the construction of the adapter 8, which may be disposable or reusable. It is provided with at least one optical window 14 for allowing the infrared radiation to be absorbed by the gas components in the measuring chamber between the optical windows. Typically there are two infrared transmitting optical windows 14. As discussed in more detail below, the infrared emitter is located on one side of the adapter and the beam splitter assembly and detectors on the opposite side in such a way that the infrared radiation is directed from the emitter, through the windows, and to the beam splitter where it gets split and reflected to the detectors.

The signals from each of the detectors get amplified and modified to reflect the concentration of the gas to be measured. As mentioned above, the measured respiratory gas components can be any IR-absorbing component, such as carbon dioxide, nitrous oxide, and different volatile anesthetic agents. All these gases absorb infrared radiation within some specific wavelength region and this region is selected using the beam splitter and a narrowband filter as will be explained later.

Figure 3:
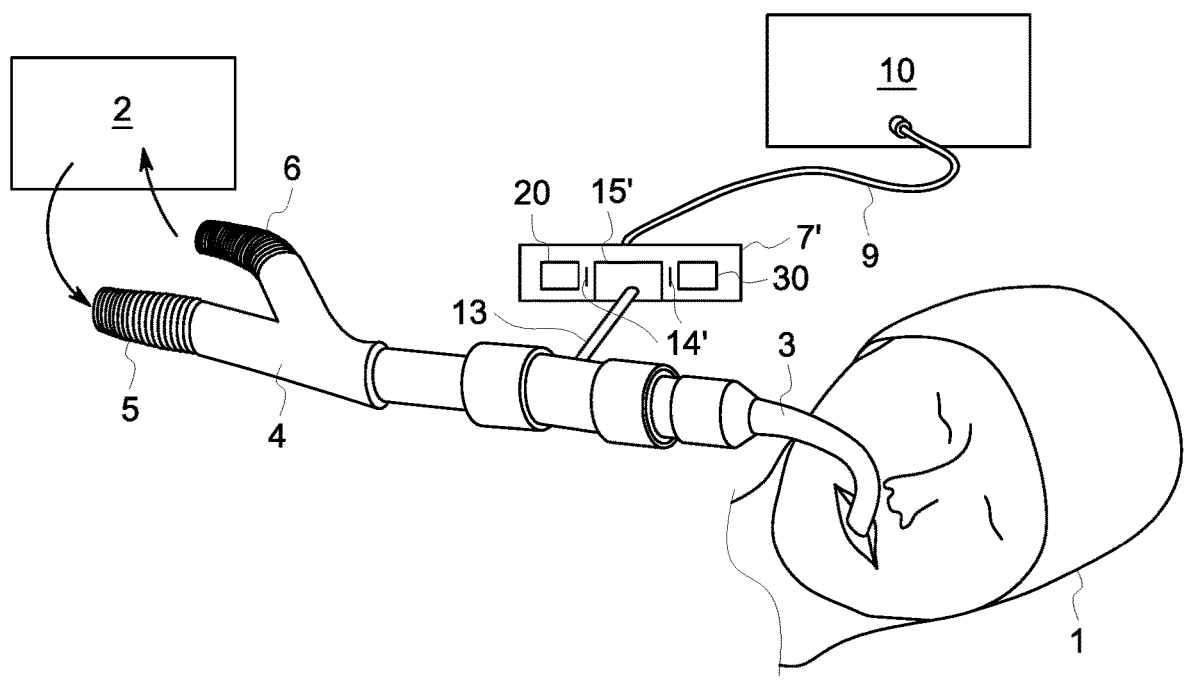
FIG. 3 illustrates a medical sidestream gas analyzer connected to the ventilation circuit of a patient.

FIG. 3 depicts a sidestream gas analyzer embodiment. In the example, the sidestream gas analyzer 7' is connected to the ventilation circuit by the gas sampling line 13. The gas sampling line 13 provides a gas sample from the patient's breathing circuit to the sidestream measurement chamber 15'. The sidestream gas analyzer 7' then measures gas concentrations of particular respiratory gasses, as is described herein. In the sidestream embodiment, the IR source 20 emits the IR wavelengths through the sidestream measurement chamber 15', such as via a window 14' on either side of a housing containing the measurement chamber. The beam splitter 30 is positioned on an opposite side of the measurement chamber 15' from the IR source 20 and is configured to reflect the IR radiation to detectors, as is described herein. The measurements by the detectors 42 and 44 (see FIG. 4) are processed and compared to determine the gas concentrations, and such information is provided to the patient monitor 10 via cable 9.

Figure 4:
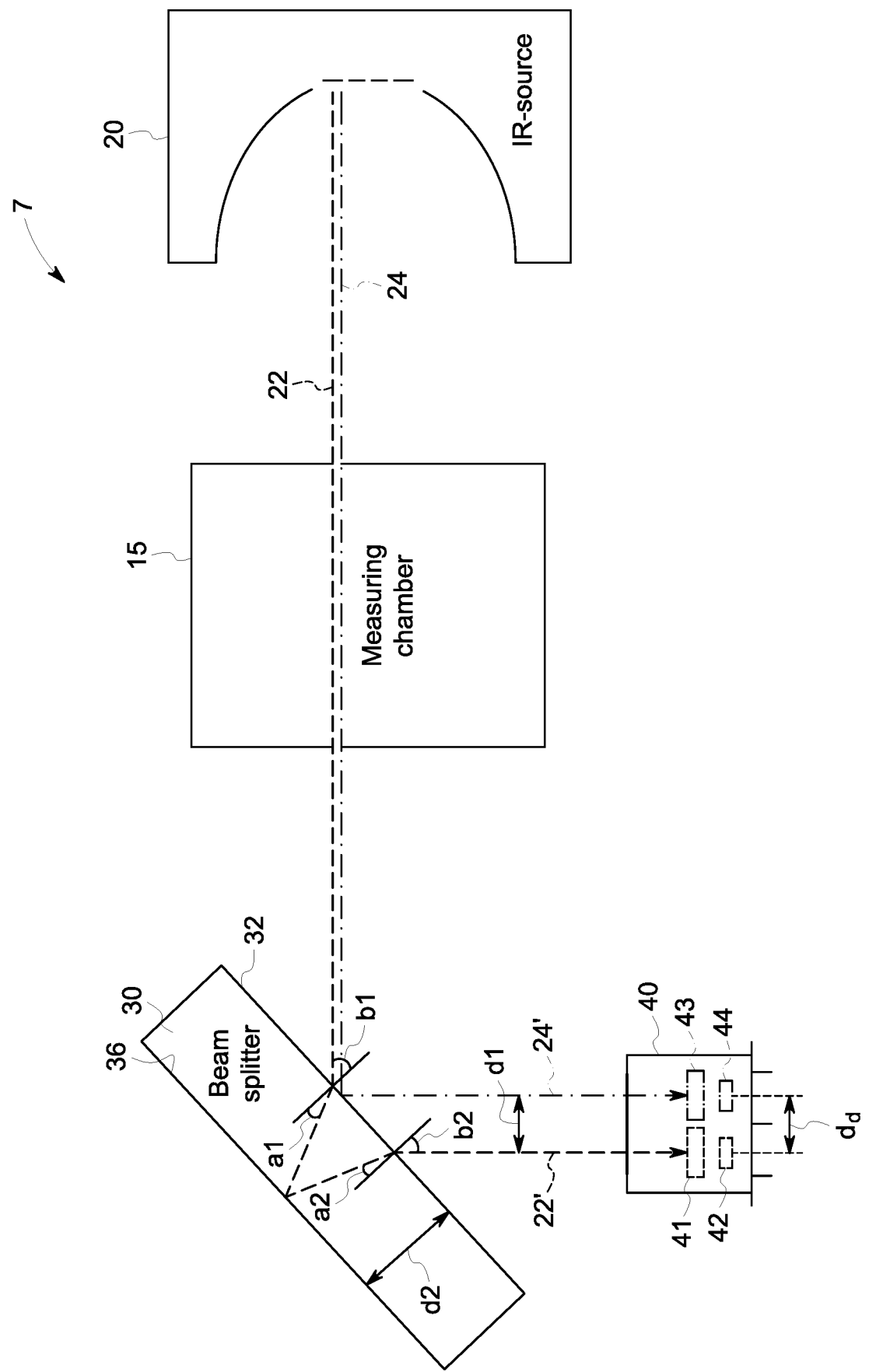
FIG. 4 schematically depicts one embodiment of a gas analyzer having a beam splitter according to one embodiment of the present disclosure.

FIG. 4 depicts an embodiment of a gas analyzer 7 according to one embodiment in the present disclosure. The depicted gas analyzer 7 can be implemented in either the mainstream embodiment depicted in FIGS. 1 and 2 or the sidestream embodiment depicted in FIG. 3. Thus, the measuring chamber 15, represented in FIG. 4 may be in the mainstream flow within the patient ventilation circuit, or may be the sidestream measurement chamber 15' shown in FIG. 3.

The IR source 20 emits two infrared wavelengths, represented in FIG. 4 as two IR beams 22 and 24. The two IR beams 22 and 24 each comprise different wavelengths of IR radiation. The infrared beams 22 and 24 travel along the same general path through the measuring chamber 15 and hit the beam splitter 30, which is on the opposite side of the measuring chamber 15 from the IR source 20. The beam splitter 30 is configured to split the two wavelengths of radiation and to reflect the first IR wavelength comprising the first beam 22 to a first IR detector 42 and to reflect the second IR wavelengths comprising the second beam 24 to a second detector 44.

Either one of the first and second beams may comprise the measurement wavelength, with the other one of the first and second beams comprising the reference wavelength. The gas measurement wavelength band is gas-specific, and the reference wavelength band is assigned accordingly. In various embodiments, the reference wavelength may be greater than or less than the measurement wavelength. The measurement wavelength and the reference wavelength may be quite close to each other, which may be desirable so that they are equally affected by the interference-inducing materials, such as moisture, mucus, blood, etc.

The beam splitter 30 comprises an IR filter 32 having a filter surface that passes one of the wavelength beams 22, 24 and reflects the other. In the depicted embodiment, the wavelength of beam 22 passes through the filter surface 32 and the wavelength of beam 24 is reflected by the filter surface 32. A mirror 36 is positioned behind the IR filter and configured to reflect the IR wavelength that is passed through the IR filter surface 32. Thus, in the example, the beam 22 is reflected by the mirror 36 in such a way that it is directed to the detector 42.

The filter 32 is configured to pass certain wavelengths and reflect others, and in various embodiments may be a high pass filter configured to pass wavelengths above a cutoff wavelength and reflect wavelengths at or below the cutoff wavelength. In other embodiments, the IR filter 32 may be a low pass filter configured to pass wavelengths below the cut off wavelength and reflect wavelengths at or above the cut off wavelength. The IR filter is designed to have a cutoff wavelength between the first IR wavelength and the second IR wavelength so as to effectively split the IR radiation emitted from the IR source based on wavelength. Thus, the beam splitter 30 is configured to provide and reflect signals having nearly full amplitude at the respective first and second wavelengths, or at least greater than 50% of the amplitude that passes through the measuring chamber 15 and reaches the beam splitter 30. In one embodiment, the beam splitter 30 is configured such that the first IR detector 42 receives at least 70% of the first IR wavelength radiation beam 22 received at the beam splitter 30 and the second IR detector 44 receives at least 90% of the second IR wavelength radiation beam 24 received at the beam splitter 30. Accordingly, the beam splitter 30 provides a greater percentage of the measurement signal to the respective detectors 42, 44 than prior art beam splitters.

In one embodiment, the IR filter 32 is comprised of sapphire having a filter depth d2. The beam splitter 30 is beneficially manufactured such that the IR filter 32 material has a depth d2 and the mirror 36 is provided on the back surface of the filter material, such as sapphire. The mirror 36 is configured to reflect as much as of the beam 22 as possible. For example, the mirror 36 may be a metal surface, such as comprised of gold, aluminum, chrome, etc.

The beam splitter 30 is configured such that, after reflection, the first IR wavelength and reflected beam 22' and the second IR wavelength in reflected beam 24' follow parallel paths separated by an offset distance d1. The depth d2 of the filter material comprising the beam splitter 30 dictates the distance d1 of the parallel paths. The beam splitter 30 and the detector set 40 must be corresponding configured such that the distance d1 aligns with a distance $d_d$ between the detectors 42 and 44, such as between the center points of the detectors.

In the depicted example, the first IR beam 22 passes through the front surface of the IR filter 32 because of its wavelength, and the second beam 24 comprising the second wavelength is reflected because of its wavelength. When the first beam 22 passes the front surface of the IR filter 32, it is refracted according to Snell's Law because air and the IR filter material 32 have different refractive indexes. Thus, the angle a1 and the angle b1 are different—i.e. the path followed by the wavelength bends when it passes through the front surface of the IR filter 32. The passed IR wavelength travels through the beam splitter to its backside, where it is reflected by the mirror 36. When the beam exits through the front surface of the IR filter 32 it is refracted again because of the different refractive indexes of the air and the IR filter. Thus, the angles a2 and b2 are different (and a1=a2 and b1=b2). At that point, the reflected first beam 22' is parallel with the reflected second beam 24', and the reflected beams 22', 24' are separated by an offset distance d1. The offset distance d1 is dependent on the IR filter material and the thickness d2 thereof.

To provide one example, where the measured respiratory gas component is $CO_2$ the measurement wavelength may be 4.26 micrometers. The reference wavelength may be higher than 4.26 micrometers, such as 5.1 micrometers, or may be lower such as 3.95 micrometers. Where the reference wavelength is lower than the measurement wavelength and the IR filter 32 is a high pass filter, the cutoff wavelength is less than 4.26 micrometers such that the measurement wavelength passes through the beam splitter 30 and the reference wavelength (which is shorter than the cut off wavelength) is reflected by the filter 32. Alternatively, the IR filter 32 may be a low pass filter which reflects wavelengths that are higher than the cut off wavelength and passes wavelengths that are lower. In an embodiment where the measurement wavelength is 4.26 micrometers and the reference wavelength is less, or shorter, the cutoff wavelength for the low pass filter is less than 4.26 micrometers but greater than the reference wavelength. In such an embodiment, the measurement wavelength is reflected by the IR filter 32 and the reference wavelength is passed. In yet another embodiment where the measurement wavelength is 4.26 micrometers and the reference wavelength is greater, the cutoff wavelength for the low pass filter is greater than 4.26 micrometers but less than the reference wavelength. Thus, in this embodiment the measurement wavelength is passed by the IR filter 32 and the reference wavelength is reflected.

The described beam splitter 30 is robust because it can be produced to comport with exacting production requirements and low tolerances given that both reflecting surfaces 32 and 36 are in the same component. Thus, no error is introduced relating to positioning two separate components. Additionally, the beam splitter 30 can be made very small, thus enabling a small gas analyzer 7. To provide one example, the detectors 42, 44 may be positioned within the detector assembly 40 such that the distance $d_d$ between their centers is 1.475 mm. The beam splitter 30 is then correspondingly constructed to reflect the first and second wavelengths to the respective detectors 42 and 44. In various embodiments, the first wavelength comprising beam 22 may be the measurement wavelength or the reference wavelength, and the second beam 24 will then be comprised of the remaining one of the measurement wavelength or the reference wavelength. In an embodiment where the first IR wavelength comprising the first beam 22 is the measurement wavelength of 4.26 micrometers (the IR wavelength that $CO_2$ absorbs), and the IR filter material 32 is sapphire, the thickness d2 will be 2.22 mm to provide an offset distance d1 between the reflected beams 22' and 24' of 1.475 mm. In a beam splitter configured for $N_2O$ measurement, the thickness d2 would be 2.18 mm, so it is practically the same as for $CO_2$.

The refractive index will be dependent on the IR wavelengths comprising the beams 22 and 24. Thus, the thickness d2 and distance d1 will also depend on the wavelength transmitted through the beam splitter 30. As will be known to a person having ordinary skill in the art, different respiratory gasses have different wavelength regions of absorption, and thus the measurement wavelength, which can be comprised in either the first beam 22 or the second beam 24, is generated accordingly. The reference wavelength is different enough from the measurement wavelength such that the beam splitter 30 can operate reliably to split the two wavelengths of radiation such that the gas measurement values are only reflected in the measurement wavelengths and are not reflected in the reference beam.

The detector set 40 is correspondingly configured to receive the reflected beams 22' and 24' comprising the measurement and reference wavelengths. IR bandpass filters 41 and 43 are positioned between the beam splitter 30 and the respective detector 42, 44, which are configured to pass the designated reference or measurement wavelengths. Either one of the first detector 42 and the second detector 44 may be configured as the measurement detector, and the other configured as the reference detector. The bandpass filters 41 and 43 are configured accordingly.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A gas analyzer for measuring a respiratory gas component, the gas analyzer comprising:
   an emitter that emits two different wavelengths of infrared (IR) radiation into a measurement chamber containing respiration gas, including a first IR wavelength and a second IR wavelength;
   a first IR detector;
   a second IR detector;
   a beam splitter configured to receive the two wavelengths of radiation emitted by the emitter and to split the two wavelengths of radiation so as to reflect the first IR wavelength to the first IR detector and reflect the second IR wavelength to the second IR detector; and
   wherein the beam splitter comprises an IR filter that is one of a high pass filter and a low pass filter having a cut-off wavelength that passes the first IR wavelength and reflects the second IR wavelength and a mirror behind the IR filter and configured to reflect the first IR wavelength.

2. The gas analyzer of claim 1, wherein, after reflection by the beam splitter, the first IR wavelength and the second IR wavelength follow parallel paths separated by an offset distance.

3. The gas analyzer of claim 1, wherein the beam splitter is configured such that the first IR detector receives at least 70% of the first IR wavelength radiation received at the beam splitter, and the second IR detector receives at least 90% of the second IR wavelength radiation received at the beam splitter.

4. The gas analyzer of claim 1, wherein the IR filter is the high pass filter and the measured respiratory gas component is $CO_2$ and the cut-off wavelength is less than 4.26 micrometers.

5. The gas analyzer of claim 1, wherein the IR filter is the low pass filter and the measured respiratory gas component is $CO_2$ and the cut-off wavelength is greater than 4.26 micrometers.

6. The gas analyzer of claim 1, wherein the IR filter is comprised of sapphire.

7. The gas analyzer of claim 6, wherein the mirror is comprised of metal.

8. The gas analyzer of claim 1, wherein the first IR wavelength is a measurement wavelength absorbed by the respiratory gas component being measured and the second IR wavelength is a reference wavelength not absorbed by the respiratory gas component being measured.

9. The gas analyzer of claim 1, further comprising:
a first IR bandpass filter positioned between the beam splitter and the first IR detector and configured to pass the first IR wavelength; and
a second IR bandpass filter positioned between the beam splitter and the second IR detector and configured to pass the second IR wavelength.

10. The gas analyzer of claim 1, wherein the measured respiratory gas component is $CO_2$ and one of the first IR wavelength and the second IR wavelength is 4.26 micrometers.

11. The gas analyzer of claim 1, wherein the gas analyzer is a mainstream gas analyzer configured such that the emitter is positioned on a first side of a mainstream sample chamber and the beam splitter is positioned on a second side of the mainstream sample chamber.

12. The gas analyzer of claim 1, wherein the gas analyzer is a sidestream gas analyzer configured such that the emitter is positioned on a first side of a sidestream sample chamber and the beam splitter is positioned on a second side of the sidestream sample chamber.

13. A beam splitter for a respiratory gas analyzer, the beam splitter comprising:
an IR filter configured pass a first IR wavelength and reflect a second IR wavelength, wherein the IR filter is one of a high pass filter and a low pass filter;
a mirror positioned behind the IR filter and configured to reflect the second IR wavelength; and
wherein the beam splitter is configured to reflect the first IR wavelength to a first IR detector and reflect the second wavelength to a second IR detector.

14. The gas analyzer of claim 13, wherein the beam splitter is configured to reflect the first IR wavelength and the second IR wavelength along respective parallel paths separated by an offset distance.

15. The gas analyzer of claim 13, wherein the IR filter is comprised of sapphire.

16. The gas analyzer of claim 13, wherein one of the first IR wavelength and the second IR wavelength is a measurement wavelength absorbed by a respiratory gas component being measured and the other one of the first IR wavelength and the second IR wavelength is a reference wavelength not absorbed by the respiratory gas component being measured.

17. A beam splitter for a respiratory gas analyzer, the beam splitter comprising:
an IR filter configured pass a first IR wavelength and reflect a second IR wavelength, wherein the IR filter is comprised of sapphire;
a mirror positioned behind the IR filter and configured to reflect the second IR wavelength; and
wherein the beam splitter is configured to reflect the first IR wavelength to a first IR detector and reflect the second wavelength to a second IR detector.

* * * * *